United States Patent
Patel et al.

(10) Patent No.: US 8,105,995 B2
(45) Date of Patent: Jan. 31, 2012

(54) SPECIFIC MILD LOW SURFACTANT, HIGH EMOLLIENT SYSTEMS WHICH RETAIN FOAMING AND PHASE STABILITY

(75) Inventors: Rajesh Patel, Middlebury, CT (US); Vivek Subramanian, Southbury, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 12/773,973

(22) Filed: May 5, 2010

(65) Prior Publication Data

US 2011/0275552 A1 Nov. 10, 2011

(51) Int. Cl.
*A61K 7/50* (2006.01)

(52) U.S. Cl. ........ 510/130; 510/121; 510/424; 510/426; 510/490; 510/499

(58) Field of Classification Search ........................ None
See application file for complete search history.

(56) References Cited

U.S. PATENT DOCUMENTS

| | | | |
|---|---|---|---|
| 6,906,016 B1 * | 6/2005 | Tsaur | 510/130 |
| 2011/0086789 A1 * | 4/2011 | Tsaur et al. | 510/129 |

OTHER PUBLICATIONS

Co-pending application for Patel et al.; U.S. Appl. No. 12/858,578, filed Aug. 18, 2010, entitled: clear Liquid Composition Comprising Alkanoyl, Glycinate, Amphoteric, Alkyl Sulfate and Specific Acrylate.

* cited by examiner

*Primary Examiner* — Necholus Ogden, Jr.
(74) *Attorney, Agent, or Firm* — Ronald A. Koatz

(57) ABSTRACT

The present invention relates to aqueous liquid compositions in which surfactant system is specifically selected so that it cleanses well, but is mild and adequately foaming. Further the composition tolerate relatively large amounts of emollient (to help mildness) while, surprisingly, showing better stability.

6 Claims, No Drawings

SPECIFIC MILD LOW SURFACTANT, HIGH EMOLLIENT SYSTEMS WHICH RETAIN FOAMING AND PHASE STABILITY

FIELD OF THE INVENTION

The present invention relates to specific mild surfactant systems with good foaming and phase stability. More specifically, the invention relates to specific, low surfactant systems in which emollients are used to preserve or enhance mildness without compromising phase stability.

BACKGROUND OF THE INVENTION

In obtaining a desirable liquid cleanser product, a variety of factors must always be considered. While cleansing, of course, is a primary objective, and is a primary reason anionic surfactants are used, the surfactant system should also be mild to the skin. In addition to mildness, however, it is also important for the formulation to foam well as foaming is often seen as a cue to the consumer of effective cleansing. Traditionally, "mild" cleansers such as Aveeno® or Cetaphil®, for example, are not effective foamers.

Amphoacetates are desirable surfactants because they help cleanse and are milder than anionic surfactants (they are, for example, amphoteric), but they typically don't foam as well as the anionics.

In selecting a mild, good foaming system, applicants have used a combination of amphoacetates and alkanoyl glycinate surfactant because, applicants have found, this combination foams better in foam lather tests than if the same amount of amphoacetates are used with commonly used alkyl sulfates (e.g., sodium lauryl ether sulfate).

Generally, to further enhance mildness of a composition, one might use an emollient(s) (e.g., water soluble humectant emollients, such as glycerin, and/or occlusive moisturizers, such as petrolatum, which block loss of water). The problem is that use of such emollients, especially in low surfactant systems, tends to destabilize phase stability (as measured, for example, by significant viscosity drops when comparing viscosity after 10 days, and having been subjected to freeze-thaw or continuous heat testing).

Quite unexpectedly, applicants have found that increasing levels of emollient to above about 10%, preferably above about 15%, not only increases the mildness of a low surfactant (e.g., less than 10%; preferably less than or equal to 8%, more preferably less than or equal to 7%) alkanoyl glycinate/amphoacetate system, but that it actually significantly enhances phase stability.

As such, applicant are able to obtain a mild composition (e.g., with mild surfactant system), but one that foams adequately, comprises high level of emollient (to further enhance mildness) and still retains stability.

BRIEF DESCRIPTION OF THE INVENTION

The present invention relates to specific low surfactant alkanoyl glycinate and amphoacetate surfactant system comprising high levels of emollient which retain good foaming compared to typical mild body washes (based, for example, on home-use test results). Further, the compositions maintain good phase stability as measured by freeze-thaw testing.

More specifically, the invention comprises specific low surfactant, high emollient compositions comprising:

1) 1-5%, preferably 2-4% by wt. salt, preferably alkali metal salt of alkanoyl glycinate;
2) 1-5%, preferably 2-4% by wt. salt, preferably alkali metal salts of amphoacetate;
   wherein total surfactant is preferably ≦10%, more preferably less than 8% by wt.
3) greater than or equal to 18%, preferably greater than or equal to 20%, more preferably 20-50% by wt. emollients selected from the group consisting of water soluble humectants (e.g., glycerin, alkylene glycol), water-insoluble occlusive emollients (e.g., petrolatum, soybean oil) and mixtures thereof;
4) 0-2%, preferably 0.1-0.5% by wt. thickening polymer (e.g., acrylate/polyacrylate copolymer); and
5) balance water.

These and other aspects features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated and that "x to y" also encompasses all ranges subsumed therein. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

DETAILED DESCRIPTION OF THE INVENTION

The present invention relates to specific mild surfactant systems which, despite presence of high levels of emollients, retain good foaming relative to other mild surfactants as measured in home-use tests. This is unexpected because emollients are often associated with depression of foam values; and mild surfactants typically foam very weakly as well. Further, the compositions maintain good phase stability. Again, this is very surprising because an increase of emollients is typically associated with phase instability.

Specifically, applicants have been able to select relatively low levels of a specific mild surfactant system, which also foams surprisingly well; while using relatively high levels of emollient (which surprisingly neither significantly decrease foam, nor destroy phase stability). This is accomplished by, as noted, using specific surfactants (specific surfactant system), using low levels of surfactant, and, quite surprisingly, using high levels of emollient.

The compositions of the invention comprise:
(a) 1-5%, preferably 2-4% by wt. salt of alkanoyl glycinate;
(b) 1-5%, preferably 2-4% by wt. salt of amphoacetate, wherein total surfactant is preferably less than 10%, more preferably less than 8% by wt. of composition;

(c) Greater than or equal to 18%, preferably greater than or equal to 20% to 50% by wt. emollient (e.g., water soluble humectants; water insoluble occlusives and mixtures thereof);
(d) 0-2%, preferably 0.1-1.5% by wt. thickening polymer (e.g., for water phase of compositions); and
(e) balance water and minors.

The invention is described in greater detail below.

Surfactant System

The surfactant system of the invention comprises combination of salt of alkanoyl glycinate and salt of amphocetate.

Specifically, the surfactant system comprises 1-5% by wt. (of total composition), preferably 2-4% by wt. salt of alkanoyl glycinate. Preferred salts include alkali metal salts of alkanoyl glycinate such as sodium cocoyl glycinate and/or alkanolamino salts such as trialkanolamine.

As is well know in the art, alkanoyl is the systematic name for group:

which is also known as an acyl group. Thus, alkanoyl glycinate is the same as acyl glycinate and represents a molecule, for example, where salt of acyl group, such as for example:

(where R may be, for example, $C_8$-$C_{24}$, preferably $C_{12}$-$C_{20}$) is combined with glycine:

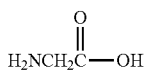

to form the alkanoyl glycinate (an amide where alkanoyl group bonds to nitrogen to form amide):

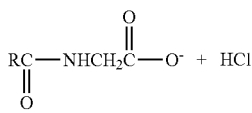

The above reaction may be conducted, for example, by an acid chloride route where R group on the acyl chloride is used to define the R group on the final alkanoyl glycinate (e.g., cocoyl glycinate if R in the acyl group is a cocoyl group).

In addition, the surfactant system comprises 1-5% by wt. preferably 2 to 4% by wt. salt of amphoacetate. Again, preferred salts include alkali metal salts such as sodium alkanoyl glycinate and/or alkanolamino salts.

It was found that this combination could be used while also maintaining good foam values relative to traditionally mild, low or no surfactant systems such as, for example, Cetaphil® or Aveeno®. In this way it is possible to obtain liquid surfactant cleanser which is both mild (measured by low loss of water in transepidermal water loss test and/or conductance tests) and mild (measured against analogous mild cleansers in home use tests).

The two surfactants comprise less than 10% by wt., preferably less than 8% by wt. of composition.

Emollients

Applicants found that liquid cleansers comprising surfactant systems as noted above unexpectedly were able to maintain good foam relative to comparable liquids, mildness (measured by TEWL tests), all while maintaining phase stability even in the presence of large amounts of emollient. Retention of stability is quite surprising because typically, when high levels of emollient are used, viscosity (associated with loss of phase stability) is significantly decreased. However, applicants found that when raising emollient levels above a certain level, quite unexpectedly the viscosity (and phase stability) were enhanced.

More specifically, the invention requires that the emollients be used at levels of greater than or equal to 18%, preferably greater than or equal to 20% up to 50% by wt. of composition. The emollient may comprise emollients which are typically found in the aqueous phase of the liquid compositions (where, for example, surfactant and water soluble thickeners are found) such as, for example, glycerin, polyalkylene glycols and mixtures thereof.

In addition, the emollient may comprise an occlusive moisturizer (typically found in the hydrophobic phase of the liquid composition, e.g., oil in water emulsion) such as, for example, petrolatum, or silicone oil. Lower viscosity occlusive oils (e.g., soybean oil) may also be used. These occlusive moisturizers are typically not water soluble according to the definition noted above.

As noted, quite unexpectedly, when the level of combined emollient was above a certain critical level, rather than experience a decrease in viscosity (and associated phase instability), an increase in viscosity (and associated stability) was found.

In preferred embodiments of the invention, the compositions of the invention also comprises a thickening agent. Such thickening agents include acrylate copolymers such as Carbopol® Ultrez 21 (or other acrylates/$C_{10}$-$C_{30}$ acrylate crosspolymers) and the like; polyethylene glycol modified glyceryl esters (e.g., PEG modified glyceryl cocoate or palmate) such as Rewoderm® LT520, etc.; modified cellulose; etc. The thickener may be present of levels of 0-2%, preferably 0.1-1.5% by wt.

In some embodiments, the liquid composition will be lamellar phase liquids and will comprise fatty acid structurant ($C_{12}$-$C_{24}$ fatty acid, particularly lauric acid), preferably at levels of 0-10%, preferably 0.1-6%, more preferably 0.1-4% by wt.

Balance of composition will comprise water; typically present in amounts of at least 30%, preferably at least 40% by wt. of composition.

In another preferred embodiment, the composition will comprise cationic polymer found in levels 0.01-3% by wt. Examples include Quatrisoft LM-200®; polyquateronium polymer (e.g., polyquaternium 24 or 39), Jaguar® type cationics, etc.

In addition, the compositions of the invention may include optional ingredients as follows:

Organic solvents, such as ethanol; auxiliary thickeners, such as carboxymethylcellulose, magnesium aluminum silicate, hydroxyethylcellulose, methylcellulose, carbopols, glucamides, or Antil® from Rhone Poulenc; perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Another optional ingredient which may be added are the defloculating polymers such as are taught in U.S. Pat. No. 5,147,576 to Montague, hereby incorporated by reference.

Another ingredient which may be included are exfoliants such as polyoxyethylene beads, walnut sheets and apricot seeds The compositions of the invention generally will have viscosity of about 50,000 to 300,000 centipoises (cps) measured using a Brookfield Viscometer with a helipath accessory and a T-bar spindle A at 0.5 RPM (measured at room temperature).

It is unpredictable and remarkable that compositions of the invention having high levels of emollients (greater than or equal to 18% by wt.), when used in defined surfactant system, have increase in viscosity after a 10 day freeze-thaw viscosity test, a measure of stability. Preferably, the compositions have increase in viscosity of greater than or equal to 10%, more preferably greater than or equal to 15% and more preferably greater than or equal to 20% relative to initial viscosity (measured as defined in protocol) prior to the test.

Further compositions of the invention preferably have transepidermal water loss (measured by TEWL test) of less than 1.60, preferably less than 1.50 grams/m²h (grams per meter squared per hour). TEWL value is the measure of water loss through skin (based on change over baseline over time as described in protocol) and is an estimate of skin's ability to retain moisture. It is typically an index of the extent of possible damage of the skin's water-barrier function. That is, higher TEWL value indicates greater water loss and this is typically consistent with increased damage of the barrier function of the stratum corneum as may occur, for example, from irritant exposure.

Finally, as show in the examples, the composition will have, both good foam lather and stability, as well as good cleansing.

The invention will now be described in greater detail by way of the following non-limiting examples. The examples are for illustrative purposes only and not intended to limit the invention in any way.

All percentages in the specification and examples are intended to be by weight unless stated otherwise.

Protocol

Measurement of Viscosity (e.g., for Stability Tests)

This method covers the measurement of the viscosity of the finished product.

Apparatus

Brookfield RVT Viscometer with Helipath Accessory;
Chuck, weight and closer assembly for T-bar attachment;
T-bar Spindle A;
Plastic cups diameter greater than 2.5 inches.

Procedure

1) Verify that the viscometer and the helipath stand are level by referring to the bubble levels on the back of the instrument.
2) Connect the chuck/closer/weight assembly to the Viscometer (Note the left-hand coupling threads).
3) Clean Spindle A with deionized water and pat dry with a Kimwipe sheet. Slide the spindle in the closer and tighten.
4) Set the rotational speed at 0.5 RPM. In case of a digital viscometer (DV) select the % mode and press autozero with the motor switch on.
5) Place the product in a plastic cup with inner diameter of greater than 2.5 inches. The height of the product in the cup should be at least 3 inches. The temperature of the product should be 25° C.
6) Lower the spindle into the product (~¼ inches). Set the adjustable stops of the helipath stand so that the spindle does not touch the bottom of the plastic cup or come out of the sample.
7) Start the viscometer and allow the dial to make one or two revolutions before turning on the Helipath stand. Note the dial reading as the helipath stand passes the middle of its downward traverse.
8) Multiply the dial reading by a factor of 4,000 and report the viscosity reading in cps.

Freeze Thaw Test

In the freeze-thaw viscosity test, protocol for measurement of viscosity is the same as the protocol for measurement of viscosity described in protocol above. According to the freeze-thaw viscosity test, samples are obtained at room temperature (about 25° C.), frozen to about −10° C. and then thawed back to room temperature in one complete cycle (one complete cycle of freezing and thawing back to room temperature was done in one day). This cycle is repeated 10 times over a 10 day period until sample is thawed to room temperature on the last day. The viscosity measurement (using protocol described above) is then taken after 10 cycles.

Heat Test

In the heating test (e.g., to test phase stability), the sample is heated to 50° C. for 10 days and the viscosity of the sample is measured using the same protocol noted above after 10 days of heating.

Home-Use Test Protocol for Lather and Lather Creaminess:

According to home use test for obtaining data on lather and lather creaminess (relative, for example, to other typical mild body washes), applicants provided compositions comprising inventive formulations (e.g., Example 3) or comparatives (e.g., Dove Sensitive Skin) to consumers to take home, and with instructions to use as they normally would use at home. Consumers were then asked to rate products, after three weeks, according to various listed attributes, including specifically for lather amount and lather creaminess. The attributes were rated on a scale of 0-7, with the higher number being indicative of better performance.

TEWL Test

Transepidermal water loss (TEWL) measurements of skin are made using Evaporimeter® (e.g., Evaporimeter 004BI) or AquaFlux® (e.g., AquaFlux 066BI) apparatus, which measures moisture content in the skin through water loss. TEWL measurements are made at baseline value, after the skin has been patted dry (optionally skin can be pre-washed before drying). Values are based on change over baseline over time and are typically measured as grams per meter squared per hour (g/m²h). Specific measurements are made using Evaporimeter or AquaFlux apparatus is noted below.

1) Take baseline measurement of area to be measured (typically, the legs), after patting dry, using Evaporimeter (004BI) or AquaFlux (006BI)'
2) Apply formulation tested (0.2 ml of test product) to a 6×6 cm area marked on tested leg or legs;
3) Wash each site with product for 10 seconds;
4) Lather remains on the skin for 90 seconds and is then rinsed off for 15 seconds;
5) Post-application measurements are taken at 1.5 hours, 3 hours and 5 hours, for a total of 4 measurements;
6) Comparisons between products are made using paired t-tests at each time point. Also, area under the curve analysis was employed as a measure of overall water loss effect. Significance was determined with the p-value set at 0.05 for both methods.

Specific Measurement Protocol is as follows:
1) Take baseline measurement of area to be measured (typically, the legs) after patting dry using Skicon 200®
2) Apply formulation test (0.2 ml of test product) to a 6×6 cm area marked on tested leg or leg;
3) Wash each site with product for 10 seconds;
4) Lather remains on the skin for 90 seconds and is then rinsed off for 15 seconds;
5) Post-application measurements are taken at 1.5 hours, 3 hours and 5 hours, for a total of 4 measurements;
6) Comparisons between products are made using paired t-tests at each time point. Also, area under the curve analysis was employed as a measure of overall moisturization effect. Significance was determined with the p-value set at 0.05 for both methods.

Cleansing Efficacy Test

In this test, each product tested was applied to six test areas on the subjects' inner forearms in a balanced-randomized design in which all tested cleansers/products were tested on each panelist. Twenty panelists were used for testing for each of the lipstick and foundation tests.
Materials tested were:
(a) Aveeno® Active Naturals (Eczema Care);
(b) Cetaphil® Gentle Skin Cleanser;
(c) Inventive Composition as noted in Examples.
Cleansing efficacy was tested against:
(a) Revlon® Colorstay Lipstick (Scarlet);
(b) Revlon Colorstay Foundation (Cappuccino).

Protocol for cleansing efficacy test was as follows:
Design/Study Plan
Panelists had baseline measurements, using a Minolta CM-2002 spectrophotometer. Makeup was then applied to the marked 3.5×2.5 $cm^2$ areas on each inner forearm. Each makeup (e.g., lipstick or foundation) was then applied. After 10 minutes (drying time) the makeup was removed. Sites were delineated on each arm for a total of six test sites per panelist. Each test site was washed with 0.5 mL of cleanser directly on the site for 30 seconds in a circular motion and then rinsed under a gentle stream of water for 15 seconds.
Panelists
A total of twenty female panelist were used for each study.
Evaluation Methods
The Minolta CM-2002 spectrophotometer with L*, a*, and b* color system was used for measurements. The instrument was set in 3-flash mode. Measurements were taken at baseline (A), on application of the makeup (B), and 10 minutes after makeup removal (C).

The percentage removal was calculated as:

$$\frac{B - C \times 100}{B - A}$$

Where $B-A=((LB-A)2+(aB-aA)2+(bB-bA)2)1/2$
And $B-C=((LB-LC)2+(aB-aC)2+(bB-bC)2)1/2$
Method of Analysis
Comparisons between products were made using paired t-tests from the Percent Removed. Significance was determined with the p-value set at 0.05.
Results are set forth in the examples.

EXAMPLES

Examples 1 and 2 and Comparatives A-D

In order to show the advantages (e.g., oil removal and stability) of using ≧18% emollient in specific composition of the invention applicant prepared the following examples.

TABLE 1

| Component | | Ex. 1 | Ex. 2 | Comp A | Comp B | Comp C | Comp D |
|---|---|---|---|---|---|---|---|
| Petrolatum | | 20% | 15% | 1.6% | 4.8% | 1.6% | 4.8% |
| Soybean oil | | — | — | 0.4% | 1.2% | 0.4% | 1.2% |
| Na cocoyl glycinate | | 2.5% | 3.75% | 2.5% | 2.5% | 3.75% | 3.75% |
| Na amphoacetate | | 2.5% | 3.75% | 2.5% | 2.5% | 3.75% | 3.75% |
| Glycerin | | 20% | 10% | 10% | 10% | 10% | 10% |
| Thickening polymer (acrylate polymer) | | 1.0% | 1.0% | 1.0% | 1.0% | 1.0% | 1.0% |
| Preservatives, minors | | 0.0075% | 0.0075% | 0.0075% | 0.0075% | 0.0075% | 0.0075% |
| Water | | | | | | | |
| | Viscosity (cps) (T-bar 0.5 speed) | 262,000 | 102,000 | 60,800 | 83,060 | 64,000 | 92,000 |
| | @RT (20-25° C.) | Y | Y | Y | Y | Y | Y |
| | @50° C. | Y | Y | Y | Y | Y | Y |
| | @4° C. | Y | Y | Y | Y | Y | Y |
| | Freeze-thaw | Y | Y | Y | Y | Y | Y |

TABLE 1-continued

| Component | | Ex. 1 | Ex. 2 | Comp A | Comp B | Comp C | Comp D |
|---|---|---|---|---|---|---|---|
| | RT/40-viscosity (10 day) | 316,000 | 144,000 | 35,000 | 48,000 | 32,000 | 41,600 |
| | % change in viscosity | +21% | +41% | −42% | −42% | −50% | −55% |

Y = Yes

As seen from the Table above, when high emollient is used (40% in Ex. 1; 25% in Ex. 2) in alkanoyl glycinate/amphoacetate surfactant systems, surprisingly, stability is enhanced (as measured by enhanced viscosity after heat testing for a 10 day period). This was measured using freeze-thaw stability test described in protocol above. For the comparatives, all of which had lower than 18% emollient, viscosity was always reduced for freeze-thaw testing.

Example 3 and Comparatives E and F

Mildness Results

In order to show that compositions of the invention are "milder" than traditionally mild compositions, applicants conducted transepidermal water loss (TEWL) tests as set forth in the protocol above. Results for TEWL test are shown in Table 2 below.

TABLE 2

| | TEWL Mean Change from Baseline | | |
|---|---|---|---|
| Components | Example 3 | Comp. E (Cetaphil) | Comp. F (Olay Butter) |
| Na cocoyl glycinate | 2.5 | | |
| Na lauryl amphoacetate | 2.5 | * | ** |
| Acrylate | 1.0 | | |
| Petrolatum | 10.0 | | |
| Glycerin | 10.0 | | |
| Lauric or other fatty acid | 0.25 | | |
| DEFI*** or other surfactant | 1.0 | | |
| Water and minor | To balance | | |

TABLE 2-continued

| | TEWL Mean Change from Baseline | | |
|---|---|---|---|
| Components | Example 3 | Comp. E (Cetaphil) | Comp. F (Olay Butter) |
| TEWL Score (Mean change from Baseline) | 1.20 g/m²h | 2.40 g/m²h | 1.83 g/m²h |

* composition of Cetaphil ® Gentle Skin cleanser (Golderma, Laboratories, Inc.), as noted from ingredients label is as follows: water, Cetyl alcohol, propylene glycol, sodium lauryl sulfate, stearyl alcohol, methylparaben, propylparaben, butylparaben
** composition of Olay ® Butter (Proctor & Gamble), as noted from ingredients label, is as follow: Water, petroleum, ammonium laureth sulfate, ammonium lauryl sulfate, sodium lauroamphoacetate, lauric acid, trihydroxystearin, fragrance, sodium chloride, guarhydroxypropyl trimonium chloride, citric acid, DMDM hydantoin, sodium benzoate, disodium edta, niacinamide, PEG-14M, *butyrospermum parki* (Shea Butter) extract, tocopheryl acetate, retinyl palmitate, vitamin B3, vitamin E, vitamin A.
*** DEFI (directly esterified fatty acid isethionate) product used may be, for example, soap bar noodles made from a combination of DEFI flakes (typically comprising fatty acyl isethionate and free fatty acid with additional fatty acid and fatty soap). Noodles may comprise, for example, 40 to 55% fatty acid isethionate and 30 to 40% fatty acid and fatty soap.

As seen from the table above, the examples of the invention have lower TEWL (transepidermal water loss) scores than either Cetaphil® or Olay Butter® indicating that they retain more water. This is an established measure of the mildness of a product.

Example 4 and Comparatives G, H, and I

Foaming Results

In order to show that compositions of the invention retain good foaming characteristics (lather amounts and lather creaminess) relative to similar products, applicants conducted home use tests (as set forth in protocol) to measure both lather and creaminess for various products versus inventive examples. In this test, consumers take home products and are intended to use them as they normally would. They were then asked about various attributes and ratings were compiled on these various attributes on a scale of 0-7. Results are set forth in Table 3 below.

TABLE 3

| Component | Example 4 | Comp. G (Dove Sensitive Skin) | Comp. H (Cetaphil ®) * | Comp. I (Aveeno ®) ** |
|---|---|---|---|---|
| Petrolatum | 10% | | | |
| Glycerol | 10% | | | |
| Na cocoyl glycinate | 2.5% | | * | ** |
| Na amphoacetate | 2.5% | *** | | |
| Directly esterified fatty isethionate (DEFI) | 1.0% | | | |
| Lauric acid | 0.25% | | | |
| Water & minors | To balance | | | |

TABLE 3-continued

| Component | | Example 4 | Comp. G (Dove Sensitive Skin) | Comp. H (Cetaphil ®) * | Comp. I (Aveeno ®) ** |
|---|---|---|---|---|---|
| | Rating from users (n = 17) or amount of lather | 4.29 | 3.54 | 2.14 | 2.31 |
| | Rating from users (n = 17) in lather creams | 4.21 | 3.62 | 1.93 | 2.38 |

* Composition A Cetaphil ® is same as for Comparative E
** Composition of Aveeno ® Eczema Care Bath Work (Johnson & Johnson), as noted from ingredients label, is as follow: water, sodium trideceth sulfate, caprylic/capric triglyceride, glycerin, sodium lauroamphoacetate, sodium chloride, oat kernel flour - *Avena Sativa*, laureth-2, guar gum-cyamopsis, sodium benzoate, guar hydroxypropyltrimonium chloride, panthenol, citric acid.
*** Composition of Dove Sensitive Skin (Dove SS) is as noted below: water, *helianthus annuus* seed oil (sunflower), sodium laureth sulfate, sodium, sodium lauroamphoacetate, cocamidopropyl betaine, glycerin, petrolatum, lauric acid, cocamide MEA, guar hydroxypropyltrimonium chloride, lanolin alcohol, fragrance, citric acid, DMDM hydantoin, tetrasodium EDTA, etidronic acid, titanium dioxide (CI 78891), PEG 30 dipolyhydroxystearate (may contain).

As seen from the rating of home-use test users (17 users were used under protocol set forth above), the examples of the invention were clearly superior in both amounts of lather and lather creaminess. Thus, as noted, the compositions of the invention are able to provide not only superior mildness (see previous example), but are able to do so without sacrificing foam lather and creaminess abilities.

Example 5 and Comparatives J and K

Cleansing Efficacy

In order to show that compositions of the invention have not only mildness, good foam and stability but are also excellent cleansers, applicant conducted make-up removal tests (for lipstick and foundation), as set forth in the protocol, against analogous compositions.

T-Test comparisons based on p-values were charted for inventive example against Cetaphil® Gentle Skin Cleanser and Aveeno® Active Naturals product and Table of Average for the three products set forth below.

Tables of Average (percent removed) (Tested against Revlon® Color Stay Lipstick)

| Cetaphil Gentle Skin Cleanser | Aveeno Active Naturals (Eczema Care) | Example 5 |
|---|---|---|
| 12.91 | 57.58 | 63.15 |

Tables of Average (percent removed) (Tested against Revlon Color Stay Foundation)

| Cetaphil Gentle Skin Cleanser | Aveeno Active Naturals (Eczema Care) | Example 5 |
|---|---|---|
| 12.01 | 40.87 | 18.89 |

A summary of conclusions is noted:
Revlon Color Stay Lipstick:
Example 5 is significantly better than Cetaphil Gentle Skin cleanser, and is parity to Aveeno product in the removal of Revlon Color Stay Lipstick.

Revlon Color Stay Foundation:
Example 5 is at parity to Cetaphil Gentle Skin Cleanser and Aveeno in the removal of Revlon Color Stay Foundation. These results are again summarized in Table 4 below.

TABLE 4

| | Example 5 | Comparative J (Cetaphil) | Comparative K (Aveeno) |
|---|---|---|---|
| Petrolatum | 10% | * | ** |
| Glycerine | 10% | | |
| Na cocoyl glycinate | 2.5% | | |
| Lauryl amphoacetate | 2.5% | | |
| Acrylate | 1.0% | | |
| Citric acid | 015-0.45 | | |
| Water & minors | To balance | | |
| % stain removal (lipstick) | 63.15% | 12.91% | 57.58% |
| % stain removal (foundation) | 18.89% | 12.01% | 40.87% |

* Composition of Cetaphil ® is same as for Comparative E
** Composition of Aveeno ® is as set forth below
Aveeno Eczema Body Wash (Market Product)
Water, Glycerin, Cocamidopropyl Betaine, Sodium Laureth Sulfate, Decyl Glucoside, *Avena Sativa* (Oat) Kernel Flour, Glycol Stearate, Sodium Lauroampho PG Acetate Phosphate, Guar Hydroxypropyltrimonium Chloride, Hydroxypropyl Trimonium Hydrolyzed Wheat Protein, PEG 20 Glycerides, Hydroxypropyltrimonium Hydrolyzed Wheat Starch, PEG 150 Pentaerythrityl Tetrastearate, PEG 120 Methyl Glucose Trioleate, Propylene Glycol, Tetrasodium EDTA, PEG 6 Caprylic/Capric Glycerides, Quaternium 15, *Coriandrum Sativum* Extract, *Elettaria Cardamomum* Seed Extract, Canmiphora Hyhrrha Extract, SD Alochol 39C, May Contain, Sodium Hydroxide, Citric Acid From the above data, it is seen that the compositions of the invention, in term of cleansing, were better or equal to products which were deficient in other ways previously shown (mildness, foam stability). The inventive example was equal or superior to Cetaphil® and at least comparable to Aveeno® in stain removal.

What is claimed is:

1. An aqueous composition comprising:
    a) 1-5% by wt. salt of alkanoyl glycinate;
    b) 1-5% by wt. salt of amphoacetate,
  wherein the total surfactant is <10% by wt. of composition;
    c) 20% to 50% emollient;
    d) 0-2% by wt. thickener; and
    e) balance water
  wherein said composition has viscosity increase of $\geq 10\%$ relative to initial viscosity after subjecting to 10 days freeze-thaw test.

2. A composition according to claim 1 wherein salt of alkanoyl glycinate and/or amphoacetate is an alkali metal salt.

3. A composition according to claim 1 wherein salt of (a) or (b) comprises 2 to 4% by wt.

4. A composition according to claim 1 wherein emollient is selected from the group consisting of glycerin, alkylene glycol and mixtures thereof.

5. A composition according to claim 1 wherein emollient is selected from the group consisting of petrolatum, silicone oil and mixtures thereof.

6. A composition according to claim 1 wherein thickener polymer is selected from the group consisting of acrylate/$C_{10}$-$C_{30}$ acrylate cross-polymers, glycol modified glyceryl esters, cellulose and mixtures thereof.

* * * * *